United States Patent [19]

Hill

[11] Patent Number: 5,531,232
[45] Date of Patent: Jul. 2, 1996

[54] METHOD OF TENDON REPAIR

[75] Inventor: Bradley B. Hill, Lexington, Ky.

[73] Assignee: University of Kentucky Research Foundation, Lexington, Ky.

[21] Appl. No.: 311,693

[22] Filed: Sep. 23, 1994

[51] Int. Cl.[6] ............................................. A61B 19/00
[52] U.S. Cl. ................................................... 128/898
[58] Field of Search ................................. 128/897, 898; 623/13

[56] References Cited

U.S. PATENT DOCUMENTS

| | | |
|---|---|---|
| 2,034,785 | 3/1936 | Wappler . |
| 3,074,408 | 1/1963 | Chester . |
| 4,043,323 | 8/1977 | Komiya . |
| 4,557,255 | 12/1985 | Goodman . |
| 4,607,620 | 8/1986 | Storz . |
| 4,836,205 | 6/1989 | Barrett .................................. 606/144 |
| 4,962,770 | 10/1990 | Agee et al. . |
| 5,025,778 | 6/1991 | Silverstein et al. . |
| 5,273,024 | 12/1993 | Menon et al. . |
| 5,353,812 | 10/1994 | Chow ....................................... 128/898 |

FOREIGN PATENT DOCUMENTS 1186203  10/1985  U.S.S.R. .............................. 128/898

OTHER PUBLICATIONS

Li, KaMing et al.; "Endoscopic Retrieval of Severed Flexor Tendons"; Journal of Hand Surgery; vol. 2A, No. 2; 278–9 Mar. 1995.

*Primary Examiner*—Angela D. Sykes
*Assistant Examiner*—Samuel Gilbert
*Attorney, Agent, or Firm*—King and Schickli

[57] ABSTRACT

A method for repairing a transected or torn flexor or extensor tendon of a finger that has retracted proximally within its protective sheath includes the steps of: (a) visually locating a distal end of the tendon within the sheath; (b) engaging the distal end of the tendon, (c) pulling the tendon distally through the sheath to a tendon mending position; and (d) repairing the tendon.

7 Claims, 2 Drawing Sheets

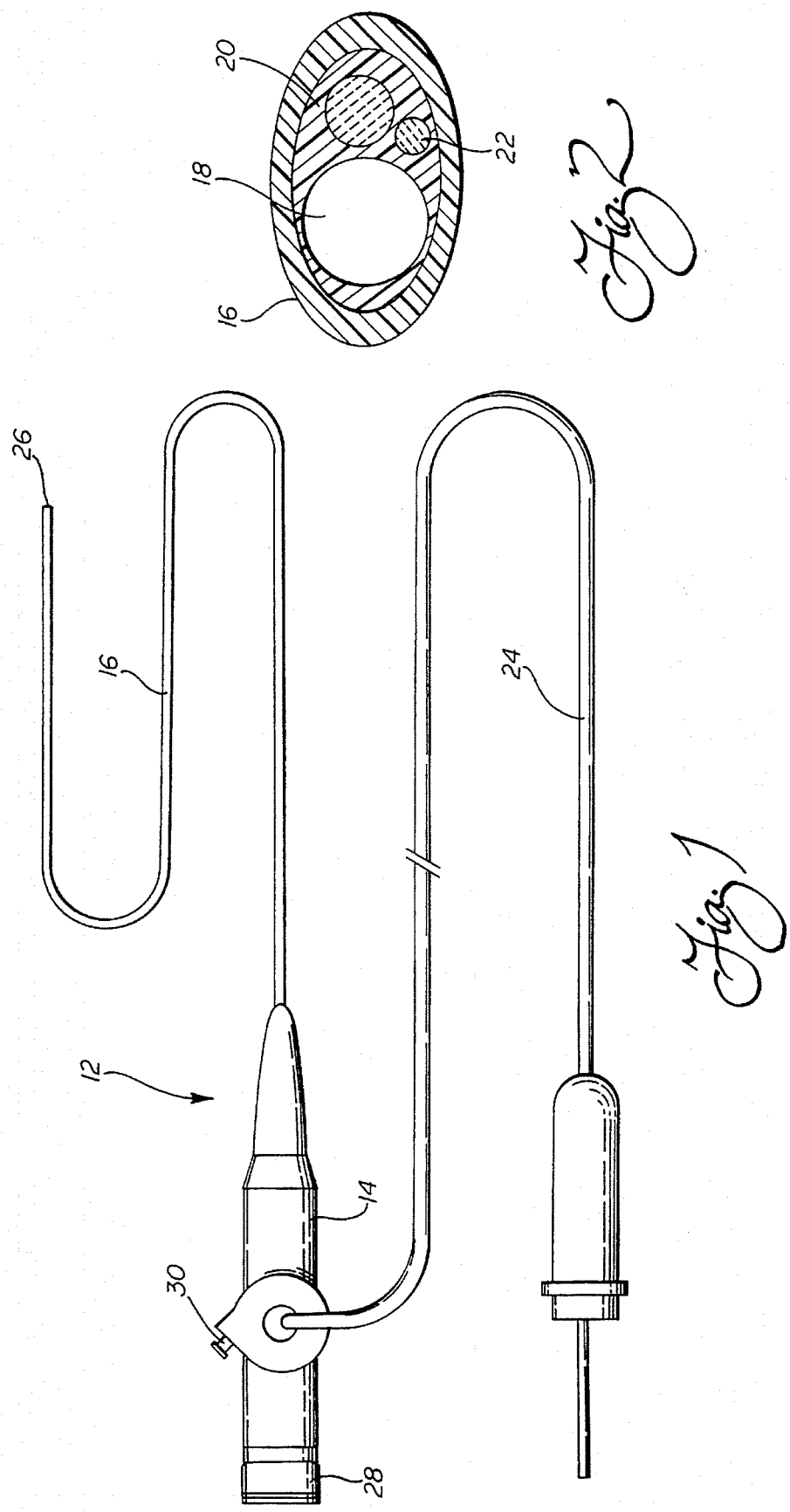

METHOD OF TENDON REPAIR

TECHNICAL FIELD

The present invention relates generally to an endoscopic surgical procedure and, more particularly, to a minimally invasive method of repairing a transected or torn flexor or extensor tendon of a finger that has retracted proximally within the associated tendon sheath.

BACKGROUND OF THE INVENTION

Flexor or extensor tendons are attached to phalangeal bones at very specific and well-localized insertion sites. The only other attachments are filamentous vincular strands. As a result of this physiological structure, transected or torn flexor or extensor tendons are prone to retract proximally within their sheaths. This tendency makes the task of tendon retrieval a difficult one often leading to tendon sheath and pulley system injury.

More specifically as an example, the flexor tendon and its delicate fibro-osseous canal depend on the preservation of smooth continuous surfaces for optimal tendon excursion during joint flexion. One consequence attending sheath disruption during tendon repair is the formation of adhesions between tendon and sheath and resulting damage to the pulley system which ultimately limits flexion or bending of the involved finger.

Doyle and Blythe describe the series of cruciate and annular pulleys that provide the mechanical advantage for optimal flexion at the interphalangeal joints (see Doyle, J. R. and Blythe, W. F. Anatomy Of The Flexor Tendon Sheath And The Pulleys Of The Thumb. *J. Hand Surge* 2:2; 149–151, 1977). The most important of these are the A2 and A4 pulleys that are responsible for holding the tendons against the shafts of the proximal and middle phalangeal bones. This structural arrangement keeps the moment arm about the PIP joint to a minimum and allows the maximal flexion at the PIP joint for a given tendon excursion distance. The cruciate pulleys are less important in the mechanical aspects of tendon function. Injury to them, however, may create adhesions between tendon and sheath that can be even more crippling than damage to the more important annular pulley structures.

Further, it should be appreciated that nutrients are known to travel to tendons via three routes: the synovial fluid around the tendon, the intrinsic vessels within the peritenon and via the long and short vincular mesenteries. Preservation of these routes requires minimal further disruption of these structures during tendon repair.

Tendon injuries for which it is most difficult to obtain satisfactory functional results are those occurring in zone 2 as described by Verdan. Zone 2 extends from the proximal end of the fibro-osseous flexor tendon sheath to the insertion of the flexor digitorum superficialis tendon at the midportion of the middle phalanx. These are the injuries that often result in the retraction of the tendon within the sheath, thereby setting the stage for lengthy dissections and further injury to facilitate tendon retrieval and repair.

A common method for tendon retrieval is flexion of the finger or digit to shorten the length of the fibro-osseous canal. In certain limited instances this procedure exposes the edge of the tendon so as to allow it to be grasped. Another technique is the blind passage of a hemostat or other clamp within the tendon sheath to grasp the tendon edge. If the tendon cannot be retrieved after three blind passes, most authorities agree that the safest and most efficacious next step is to dissect out the tendon sheath. It should be appreciated, of course, that the unsuccessful blind passes only further traumatize the sheath and possibly the tendon. The subsequent dissection causes still further trauma.

Another method used by many experienced hand surgeons involves the making of a counter incision proximal to the site of injury, usually in the palm, to identify the involved tendon. That tendon is then attached to a guide catheter and passed distally through the tendon sheath where repair is completed.

While the above-described state of the art techniques usually provide access to the tendon for purposes of repair each, unfortunately, further traumatizes the tendon, risks injury to digital vessels and nerves from incisions and causes injury to soft tissue with loss of normal flaps. A need is therefore identified for an improved approach for repairing transected or torn flexor or extensor tendons of the fingers.

SUMMARY OF THE INVENTION

Accordingly, it is a primary object of the present invention to provide a method for repairing a transected or torn flexor or extensor tendon of a digit, preferably a finger but including a toe, that has retracted proximally within its sheath that overcomes the above-described limitations and disadvantages of prior art approaches.

Another object of the present invention is to provide a relatively simple procedure for repairing transected or torn flexor or extensor tendons that is minimally invasive thereby causing less iatrogenic injury to normal tissues. Advantageously, incisions from the procedure are smaller and less painful with less potential for scar and contracture formation. Further, because smaller incisions are utilized, there is less potential for serious wound infections. Tissue reaction and adhesion formation are also decreased with less trauma to the delicate tendon sheath. This results in improved healing and rehabilitation. Better preservation of the pulley system is also provided. This advantageously leads to a better functional outcome and potentially less need for further corrective medical procedures including tenolysis and secondary pulley reconstruction.

Still another object of the present invention is to provide an improved method of repairing transected or torn flexor or extensor tendons of the digits utilizing an endoscope in the repair operation. Advantageously, the resulting improvements in the functional outcome mean that the patients will have less long term disability and a higher percentage will return as productive members of the work force. Advantageously, the procedure may be completed in a relatively short period of time thereby decreasing operating time and anesthesia costs. All of these points, of course, are to the mental well-being and economic benefit of the patient.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved method is provided for repairing a transected or torn flexor or extensor tendon of a finger or toe that has retracted proximally within its sheath. As generally defined, the method includes the step of visually locating a distal end of the tendon within the sheath, engaging the distal end of the tendon, pulling the tendon distally through the sheath and repairing the tendon.

In accordance with the present method the distal end of the tendon is located within its sheath by utilizing an endoscope. More specifically, the method includes a step of positioning the distal end of the endoscope within the tendon sheath. The endoscope is then passed through the lumen of the tendon sheath until it is possible to visually confirm the location of the distal end of the tendon within the sheath. This is accomplished by viewing through a fiber optic bundle and objective lens in an observation lumen in the endoscope.

The distal end of the tendon is then engaged by passing a grasping tool, such as forceps, through a working channel in the endoscope. While viewing the procedure, the distal end of the tendon is carefully grasped with the grasping tool. The tendon is then pulled by withdrawing the endoscope from the tendon sheath while the grasping tool is attached to the distal end of the tendon. Once the tendon is pulled to the mending position (i.e. site of the injury) the tendon is reattached or reconnected to provide repair.

Advantageously, the present method does not require dissection of the tendon and, as a result, tendon sheath disruption is generally minimized. Thus, the ancillary injuries characteristic of prior art repair approaches including the formation of adhesions between tendon and sheath and damage to the pulley system that ultimately limits flexion of the involved finger are advantageously minimized or substantially eliminated. Hence, the present invention represents a significant advance in the art.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention and together with the description serves to explain the principles of the invention. In the drawing:

FIG. 1 is a side elevational view of an endoscope that may be utilized in the method of the present invention to repair a transected or torn flexor or extensor tendon;

FIG. 2 is a cross-sectional view of the flexible catheter of the endoscope; and

Figure 3:
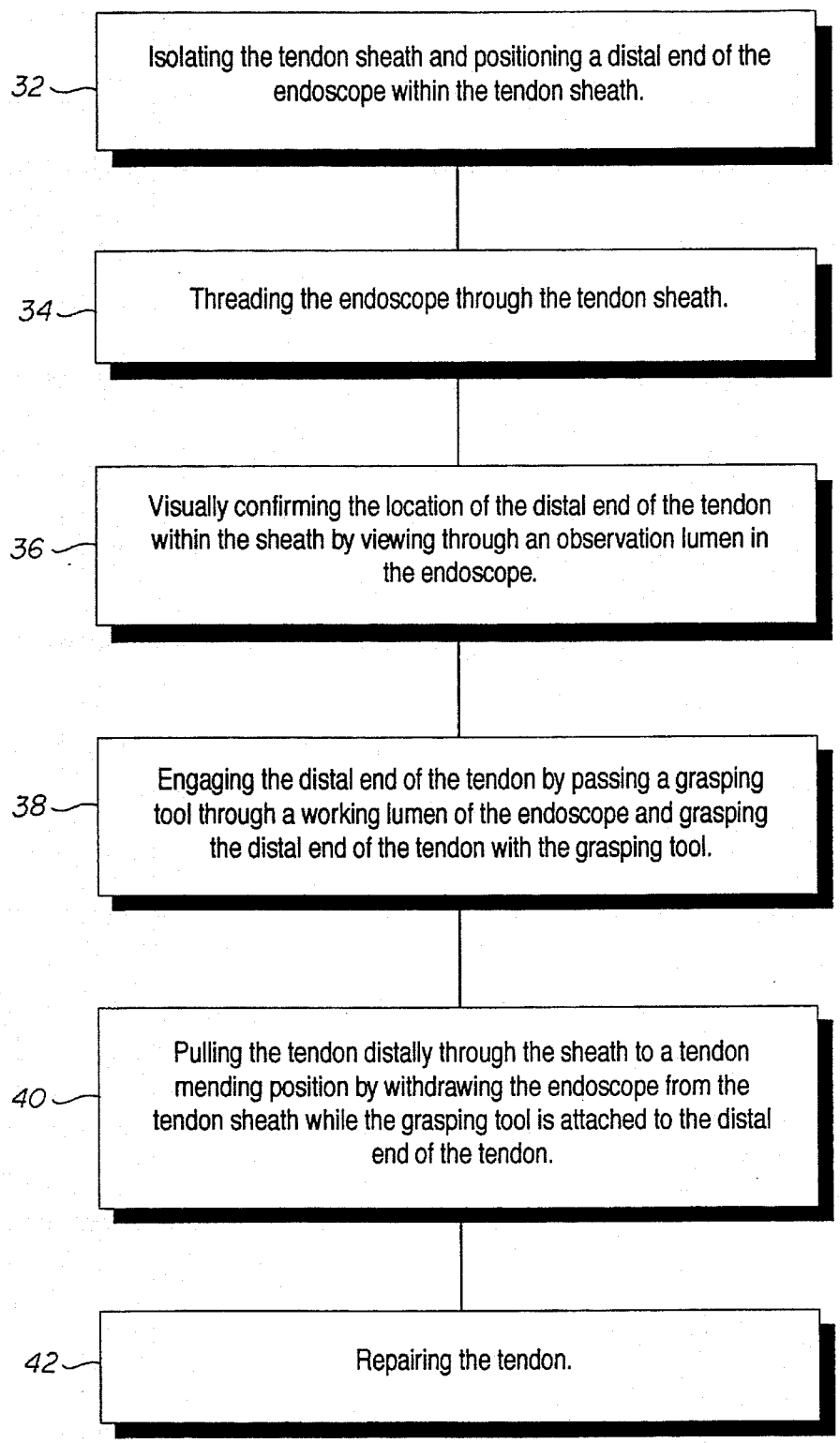
FIG. 3 is a schematical block diagram describing the steps of the method of the present invention.

Reference will now be made in detail to the present preferred embodiment of the invention, an example of which is illustrated in the accompanying drawing.

DETAILED DESCRIPTION OF THE INVENTION

Reference is made to FIGS. 1–3 that serve to illustrate the method 10 of the present invention of repairing a transected or torn flexor or extensor tendon of a digit (i.e. either a finger or a toe) that has retracted proximally within an associated tendon sheath. The method 10 may be generally described as including the steps of visually locating a distal end of the tendon within its sheath, engaging the distal end of the tendon, pulling the tendon distally through the end of the sheath to a tendon mending position and repairing the tendon.

As will become apparent as the description hereof proceeds, the method relies upon the utilization of an endoscope. This allows the tendon to be repaired in a minimally invasive manner thereby substantially reducing or eliminating the formation of adhesions between tendon and sheath and damage to the pulley system that ultimately limits the flexion of the involved finger. While the method is being described with respect to the repair of a flexor tendon, it should be appreciated that it is equally applicable to the repair of an extensor tendon.

An endoscope 12 such as may be utilized in the present method 10 is shown in FIGS. 1 and 2. The endoscope 12 includes a head assembly 14 at its proximal end that is operatively connected to a flexible catheter 16. As best shown in FIG. 2, the flexible catheter 16 includes three separate components; a working channel 18, a viewing lumen 20 holding a fiber optic bundle and objective lens, and a light path/guide 22.

As is further known in the art, a universal light guide 24 is operatively connected to the head assembly 14 so as to be in communication with the light path/guide 22. The universal light guide 24, may be connected to a fiber optic light source (not shown). Light from the light source is communicated through the universal light guide 24 and the light path/guide 22 to the tip 26 of the flexible catheter 16.

An eyepiece 28 is also operatively connected to the head assembly 14. Eyepiece 28 communicates with the fiberoptic bundle and objective lens in the viewing lumen 20 of the flexible catheter 16. Accordingly, it is possible through the eyepiece 28 and fiberoptic bundle and objective lens of the viewing lumen 20 to view structures adjacent to the tip 26 of the flexible catheter 16 that are illuminated by means of the light source in the manner just described.

Head assembly 14 also includes a working channel port 30 that is in communication with the working channel 18 in the flexible catheter 16. Wire-like instruments may be passed through the working channel port 30 and working channel 18 and extended from the tip 26 of the flexible catheter 16. In this manner, a grasping tool such as forceps may be passed through the endoscope 12 to grasp a selected structure (e.g. distal end of a flexor tendon) as will be described in greater detail below.

The method 10 of the present invention is best illustrated with reference to FIG. 3. The method includes the initial step 32 of isolating the tendon sheath and carefully positioning the distal end or tip 26 of the endoscope 10 within the tendon sheath. Preferably, the tendon sheath is isolated adjacent the site of the injury. To do this it may be necessary to make a small transverse incision across the sheath so as to clearly expose the sheath in cross-section. The need for such an incision is actually determined by the nature of the injury being repaired.

Next is the step 34 of threading the flexible catheter 16 of the endoscope 12 through the tendon sheath. More specifically, the flexible catheter 16 is slowly advanced into the lumen of the tendon sheath. During this threading operation, the doctor carefully manipulates the endoscope 12 to avoid trauma and injury to the tendon sheath. Further, the doctor may continuously view the interior of the tendon sheath by looking through the eye piece 28 so as to confirm the presence or absence of any additional ancillary injury to, for example, the pulley system that may require repair.

Next is the step 36 of visually confirming the location of the distal end of the tendon within the sheath. As previously described, this is done by viewing through the eyepiece 28 and the fiberoptic bundle and objective lens of the observation or viewing lumen 20 in the endoscope 12.

This is followed by the step 38 of engaging the distal end of the tendon by passing a grasping tool such as forceps through the working channel 18 of the endoscope 12 and grasping the distal end of the tendon with the grasping tool. This is then followed by the step 40 of pulling the tendon distally through the sheath to a tendon mending position adjacent the injury site. More specifically, this is accomplished by slowly and carefully withdrawing the flexible catheter 16 of the endoscope 12 from the tendon sheath while the grasping tool is attached to the distal end of the tendon.

With the tendon held in the mending position, the step 42 of repairing the tendon is completed. More specifically, where the tendon has been severed in two, the two severed ends of the tendon are connected together by any appropriate means known in the art to be suitable for this purpose. Where the tendon has actually become detached from the phalangeal bones, appropriate reattachment is made again by any means known in the art to be suitable for this purpose. The incision is then closed in accordance with standard medical procedures.

Advantageously, the present method is minimally invasive. Accordingly, there is minimal tendon sheath disruption during the repair method. As a result, the formation of adhesions between tendon and sheath and damage to the pulley system are minimized or eliminated. The routes for the travel of nutrients by means of the synovial fluid around the tendon, intrinsic vessels within the peritenon and via the long and short vincular mesenteries are also maintained with minimal disruption. This significantly aids in the healing process. Further, a smaller and less painful incision is required. Accordingly, there is less potential for scar and contracture formation as well as serious wound infection. Overall healing and rehabilitation are significantly shortened, pain is reduced and a better functional outcome generally results thereby significantly reducing the potential need for further medical procedures such as tenolysis and secondary pulley reconstruction.

In summary, numerous benefits result from employing the concepts of the present invention. As pointed out above, the present method provides a number of significant advantages over state of the art approaches now utilized to repair transected or torn flexor or extensor tendons of the finger that have retracted proximally within the tendon sheaths. The better functional outcomes that are achieved means that patients will have less long-term disability and a higher percentage will be able to return to the work force as productive members. Fewer redo operations and follow-up procedures will be required thereby saving thousands of dollars in medical expenses. In all, the present invention represents a very significant advance in the art of tendon repair.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with breadth to which they are fairly, legally and equitably entitled.

I claim:

1. A method of repairing a transected or torn flexor or extensor tendon of a digit that has retracted proximally within an associated tendon sheath, comprising the steps of:

visually locating a distal end of the tendon within the sheath;

engaging the distal end of the tendon;

pulling the tendon distally through the sheath to a tendon mending position; and repairing the tendon.

2. The method as set forth in claim 1, wherein the distal end of the tendon is located by utilizing an endoscope.

3. The method set forth in claim 1, including isolating the tendon sheath and positioning a distal end of the endoscope within the tendon sheath.

4. The method set forth in claim 3, including threading the endoscope through the tendon sheath.

5. The method set forth in claim 3, including viewing the distal end of the tendon through the endoscope while engaging the distal end of the tendon.

6. The method set forth in claim 3, wherein the distal end of the tendon is engaged by passing a grasping tool through a working channel in the endoscope and grasping the distal end of the tendon with the grasping tool.

7. The method set forth in claim 6, wherein the tendon is pulled to said tendon mending position by withdrawing the endoscope from the tendon sheath while the grasping tool is attached to the distal end of the tendon.

* * * * *